United States Patent [19]

Viñas

[11] Patent Number: 5,208,254
[45] Date of Patent: May 4, 1993

[54] PROCESS FOR THE PREPARATION OF ZINC CARBOCYSTEINATE COMPOSITIONS

[75] Inventor: Antonio B. Viñas, Barcelona, Spain

[73] Assignee: Laboratorios Vinas, S.A., Barcelona, Spain

[21] Appl. No.: 689,695

[22] Filed: Apr. 19, 1991

[30] Foreign Application Priority Data

Jul. 13, 1990 [ES] Spain ................................. 9001921

[51] Int. Cl.$^5$ .......................................... A61K 31/315
[52] U.S. Cl. .................................... 514/494; 514/838; 514/893; 514/894
[58] Field of Search ............... 514/494, 562, 838, 893, 514/894

[56] References Cited

U.S. PATENT DOCUMENTS 3,326,762 6/1967 Joullie et al. ...................... 514/562
4,618,625 10/1986 Vinas .................................. 514/494

OTHER PUBLICATIONS

Chemical Abstracts 106(15):118565, Labadie et al. (1986).
Chemical Abstracts 111(13):109014, Dadhich et al. (1989).

Primary Examiner—Frederick E. Waddell
Assistant Examiner—Raymond J. Henley, III
Attorney, Agent, or Firm—Flynn, Thiel, Boutell & Tanis

[57] ABSTRACT

A process for the preparation of a zinc carbocysteinate composition useful in the treatment of hepatopathies, comprising the steps of combining a therapeutically effective amount of zinc carbocysteinate with appropriate vehicles or excipients, and wetting, stirring, sieving and drying the combined zinc carbocysteinate to form unit dosages of the zinc carbocysteinate composition for oral administration.

6 Claims, No Drawings

PROCESS FOR THE PREPARATION OF ZINC CARBOCYSTEINATE COMPOSITIONS

The present invention relates to a process for the preparation of zinc carbocysteinate compositions, as well as to the use of them in the prophylaxis or treatment of acute and chronic hepatopathies of diverse etiologies.

Zinc carbocysteinate (zinc carboxymethylcysteinate), of formula:

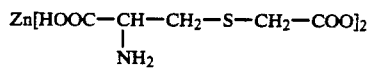

has been described as an effective compound in the treatment of skin diseases, including seborrhea, alopecia, greasy hair, exfoliative dermatitis, acne, brittle nails, and the like, and also in the treatment of respiratory diseases (U.S. Pat. No. 4,618,625).

Hepatopathies constitute a serious world problem. Epidemiological studies carried out in the USA show that cirrhosis is the eighth greatest cause of mortality (13.6 deaths per 100,000 inhabitants), and occupies the fourth and fifth place in men and women, respectively, during the most productive decades of life (35–54 years). Accordingly, the appearance of a new treatment in this field is of great interest, especially if its formulation is well tolerated in both the short and the long term.

Among hepatopathies, the following stand out:
a) Alcoholic hepatopathy, including: fatty liver (hepatic steatosis), alcoholic hepatitis and alcoholic cirrhosis.
b) Chronic hepatitis: active and persistent.
c) Hepatic cirrhosis: alcoholic, following hepatitis (B; non-A, non-B), metabolic—Wilson's disease and primary biliary cirrhosis.

To assess the seriousness of these conditions, a distinction should be made between cirrhotic and noncirrhotic hepatopathies. Cirrhosis, by definition, is a chronic, diffuse and irreversible process. Its prognosis will vary according to the presence or absence of some complication. More than 50% of cirrhotic patients who have not yet shown a complication die after 10 years. Once a complication has appeared, the prognosis of the cirrhosis becomes distinctly less favorable.

The immediate mortality from alcoholic hepatitis fluctuates between 10 and 20% of cases. The possibility of transition to hepatic cirrhosis is dependent on whether or not the intake of alcohol persists.

The prognosis of active chronic hepatitis is uncertain. Left to follow its natural course, the disease usually ends, other than in rare exceptional cases, in hepatic cirrhosis.

To date, there is no specific treatment for hepatopathies (except corticoids for active chronic hepatitis). There is consequently no medication capable of modifying the natural history of the disease. All treatment is based on adopting symptomatic measures and eliminating triggering factors such as alcohol.

Given this state of the art, the object of our invention is understood, we have discovered that zinc carbocysteinate is very effective in the prophylaxis and treatment of hepatopathies. Thus, the object of the present invention is to provide a medicinal product which is useful, that is to say effective and nontoxic, in the prophylaxis or treatment of acute and chronic hepatopathies of diverse etiologies, especially in alcoholic hepatopathy, chronic hepatitis and hepatic cirrhosis. This medicinal product consists of a composition in which zinc carbocysteinate (A-177) is the main active principle.

It is also an object of the present invention to provide a process for preparing a composition for the prophylaxis or treatment of hepatopathies, in which A-177 is combined with carbohydrates such as corn starch or its derivatives, sucrose or lactose, with polyvinylpyrrolidone or cellulose derivatives, or natural gums, and with calcium salts such as calcium phosphate and carbonate.

The combination obtained is subsequently wetted with a solution of polyoxyethylenated sorbitan esters, such as the monooleate, stearate, laurate and palmitate, and polyethylene glycol 4000 or 6000, in water and organic solvents such as ethyl alcohol.

The wet mass is sieved and subsequently subjected to drying in an oven at 40° C. for 18 to 24 hours.

Finally, talc or other silicates, synthetic sweeteners such as saccharin and flavorings are added.

It is also an object of the present invention to provide a process for preparing zinc carbocysteinate in which the percentage of A-177 with respect to the total content is from 50 to 80%.

When put into pharmaceutical dosage forms, the compositions obtained may be administered by conventional methods in solid form (tablets, capsules, dragees or single-dose sachets) or liquid form (syrups or ampuls for oral administration). The zinc carbocysteinate compositions have been studied in pharmacological models of hepatopathies, also testing clinically for tolerability and activity of daily dosages containing between 100 and 1200 mg of A-177, divided into one or more doses, depending on the dosage. Preferably, the usual dosage varies between 150 and 400 mg/day.

All the results of the examples show prophylactic and curative effects of zinc carbocysteinate in hepatopathies. These results are advantageous and surprising, since it is not possible to link them directly with those recorded in dermatology or in the treatment of respiratory infections which are already known in the prior art.

EXAMPLE 1

Preparation of a Zinc Carbocysteinate Composition 72 kg of zinc carbocysteinate was combined with 19 kg of corn starch and 1.4 kg of polyvinylpyrrolidone and stirred for 20 minutes. The resulting solid was wetted with an aqueous-alcoholic solution (1.2 parts of water and 2.5 parts of 96° strength ethyl alcohol) in which 3.800 kg of polyethylene glycol 4000 and 0.060 kg of polyoxyethylenated sorbitan monooleate was dissolved. This step was carried out under continuous stirring for 30 minutes.

The wet mass was sieved (No. 3 screen) and dried in an oven at 40° C. for 18 to 24 hours The residue was sieved again (No. 6 screen).

2 kg of talc and 1.600 kg of sodium starch glycolate was added and the mixture stirred for 15 minutes.

The combination thus prepared was distributed in 500 mg single doses.

EXAMPLE 2

Preparation of a Zinc Carbocysteinate Composition 75 kg of zinc carbocysteinate was combined with 12 kg of calcium phosphate dihydrate, 7.6 kg of corn starch, 1 kg of polyvinylpyrrolidone and 0.002 kg of saccharin sodium and stirred for 25 minutes.

The resulting solid was wetted with an aqueousalcoholic solution (1.2 parts of water and 2.5 parts of 96° strength ethyl alcohol) in which 0.020 kg of polyoxyethylenated sorbitan monooleate was dissolved. This step was carried out with continuous stirring for 30 minutes.

The wet mass was sieved (No. 6 screen) and dried in an oven at 40° C. for 18 to 24 hours.

2 kg of talc, 2 kg of sodium starch glycolate and 0.008 kg of mint essence was added to the residue and the mixture stirred for 20 minutes.

The combination thus prepared could be administered orally at single doses of 480 mg.

EXAMPLE 3

Activity in Hepatic Cirrhosis

1) Protocol

Male Wistar rats, body weight 210±20 g at the beginning of the trial, was used as experimental animals.

Hepatic cirrhosis was induced by means of intraperitoneal injection of a solution of $CCl_4$ in vegetable oil (1:1), which was administered at a dose of 1.5 ml/kg 3 times a week for 30 days.

3A) Preventive Effect

In this trial, A-177 was administered simultaneously with $CCl_4$. The following groups of animals were established:

I—Control, receiving vehicle; II—Cirrhosis, receiving $CCl_4$; III—A-177; IV—A-177+$CCl_4$.

A-177 was administered orally in the form of a suspension.

3B) Curative Effect

In this trial, administration of A-177 was begun when the period of induction of cirrhosis was complete, its effect on recovery of the hepatic lesions being evaluated in this case. The following groups of animals were established:

I—Control, cirrhosis; II—Control, 2 days' recovery; III—A-177, 2 days' recovery; IV—Control, 4 days' recovery; V—A-177, 4 days' recovery; VI—Control, 7 days' recovery; VII—A-I77, 7 days' recovery.

2) Sacrifice of the Animals and Evaluation of Biochemical and Morphological Parameters Throughout the treatment period, the weight of the animals was monitored, the condition of the latter and possible incidents such as icterus, ascites, and the like, likewise being noted.

When the treatment period had ended, the rats were sacrificed by decapitation and total exsanguination. Dissection of the liver was then performed for subsequent microscopic examination and the obtaining of samples.

From the samples obtained, the following parameters are determined:

1) In serum: transaminases (GOT and GPT), LDH, glucose and amino acids.

2) In liver: total weight, total glycogen and mobilization of the latter on fasting, total lipids, proteins, hydroxyproline and $\beta$-hydroxybutyrate. A histopathological study of the hepatic lesions, with assessment of the degree of fatty degeneration, inflammation and fibrosis, was likewise carried out.

Results

3a) Preventive Effect

Dosage: A-177, 150 mg/kg/day administered in the form of a suspension.

Table 1 shows the modifications of the glycogen levels, per gram of tissue and total, respectively. Table 2 shows the changes induced by the various treatments in the hydroxyproline levels

TABLE 1

Modifications of the hepatic glycogen levels in cirrhotic rats, control and treated with A-177

| | Control | $CCl_4$ | A-177 | $CCl_4$ + A-177 |
|---|---|---|---|---|
| mg/g | 61.3 ± 0.4[a] | 30.5 ± 0.5[b] | 56.8 ± 0.5 | 39.1 ± 0.6 |
| total, g | 0.98 ± 0.07 | 0.36 ± 0.09[b] | 0.89 ± 0.09 | 0.60 ± 0.09 |

[a] $\bar{x}$ ± s.e.m.
[b] $p < 0.001$ vs control

TABLE 2

Hepatic hydroxyproline levels in cirrhotic rats, control and treated with A-177

| | Control | $CCl_4$ | A-177 | $CCl_4$ + A-177 |
|---|---|---|---|---|
| Fed | 0.19 ± 0.02[a] | 0.82 ± 0.12[b] | 0.21 ± 0.02 | 0.46 ± 0.06[c] |
| Fasted | 0.64 ± 0.05 | 1.06 ± 0.15 | 0.57 ± 0.05 | 0.79 ± 0.18 |

[a] μmol hydroxyproline ($\bar{x}$ ± s.e.m.)
[b] $p < 0.001$ vs control;
[c] $p < 0.01$ vs $CCl_4$ As regards to the histopathological observations, the animals treated with A-177 simultaneously with $CCl_4$ exhibited a lesser degree of fibrosis than untreated cirrhotic animals.

3B) Curative Effect

Dosage: A-177, 150 mg/kg/day administered in the form of a suspension.

It was observed that the functioning of the liver was recovered very rapidly in the control animals, so that many parameters normalize a few days after administration of the $CCl_4$ was stopped. For this reason, it would be difficult to observe large differences between the control group and those treated with A-177 with respect to some parameters. Nevertheless, in some of the latter, differences were observed between control and treated animals. This was the case with the glycogen levels, both the total and those mobilized during fasting, and the $\beta$-hydroxybutyrate level, the values of which in the groups treated with A-177 were very close to those of the controls, while they remained modified in the untreated groups.

Morphological study of the livers revealed that, at the microscopic level, there are large differences in the degree of recovery of the tissue between the control animals and those treated with A-177, especially regarding fibrosis. On day 2 of the recovery, differences between the controls and rats treated with A-177 were barely discernible, a substantial degree of fibrosis being observed in both groups of animals. On day 4 of recovery, the differences were greater, livers of the treated group in which fibrosis had disappeared almost completely and the morphology of the hepatic lobuli being practically normal was observed in some cases. A regression of vacuolization and of leukocyte infiltration was likewise observed, although the differences between the control and A-177 was not as obvious in these two aspects, being a parameter which normalizes spontaneously. On day 7 of recovery, no greater differences was observed between the control and treated animals than were detected on day 4.

These results show the prophylactic and curative effects of zinc carbocysteinate in hepatopathies.

EXAMPLE 4

Clinical Tolerance

The absence of toxicity of zinc carbocysteinate was studied in compositions suitable for oral administration to humans.

The study of clinical/biological tolerance was carried out in healthy volunteers with the object of checking and assessing the local and systemic tolerability of zinc carbocysteinate by clinical and biological methods. The treatment period was 2 months. The following dosage regimens were tested:

180 mg/day, in a single dose after the evening 360 mg/day, in two doses, one after lunch and the other after the evening meal (12 volunteers).

720 mg/day, in two 360 mg doses, one after lunch and the other after the evening meal (12 volunteers).

1080 mg/day, in three 360 mg doses, after breakfast, lunch and the evening meal (12 volunteers).

Clinical and laboratory checks were carried out on days 0, 30 and 60. Biochemical parameters included serum glucose, urea, creatinine, uric acid, total bilirubin, total proteins, total cholesterol, GOT, GPT, $\gamma$-GT and prothrombin time. A complete hemogram (red cells, hematocrit, hemoglobin, mean corpuscular volume, mean corpuscular hemoglobin, erythrocyte sedimentation rate, leukocytes, differential leukocyte count and platelet count) was also performed. Analysis of urine and sediment was likewise carried out.

From the clinical standpoint, dosages of 180 mg/day and 360 mg/day in two doses were perfectly tolerated. One patient who received the dosage of 720 mg/day in two 360 mg doses reported gastric discomfort during the last 10 days of treatment, 30 minutes after taking A-177. Another two patients reported temporary mild diarrhea lasting 3 days, and moderate constipation lasting one week which also disappeared spontaneously. Lastly, in the group treated at the dosage of 1080 mg/day in three 360 mg doses, 2 cases of transient nausea after taking A-177 in the morning (lasting 3 and 6 days) and 2 cases of abdominal discomfort with flatulence and sluggishness (lasting 5 and 15 days, respectively) were recorded, cessation of the treatment in no case was required.

At the laboratory level, none of the subjects in the study exhibited adverse effects, since the biochemical and hematological parameters at completion of the treatment were in no case significantly different from those of the baseline control.

These results show that the hematological and biochemical tolerability of A-177 was excellent, and that local tolerability was optimal at a dosage of 180 mg/day and 360 mg/day (in two 180 mg doses) and good at those of 720 mg/day (in two 360 mg doses) and 1080 mg/day (in three 360 mg doses).

EXAMPLE 5

Activity in Alcoholic Hepatitis

Clinical trials in 15 patients with alcoholic hepatitis, diagnosed clinically and biochemically and by means of liver biopsy, were carried out with the object of checking the response to treatment with 720 mg/day of A-177 (in two 360 mg doses) for 4 to 6 months.

Results

Following the treatment, a general clinical improvement of the patients and a significantly favorable change in the GOT, GPT, $\gamma$-GT and bilirubin parameters were discerned.

EXAMPLE 6

Activity in Hepatic Cirrhosis

Clinical trial in 10 patients diagnosed as having compensated hepatic cirrhosis and treated with 360 mg/day of A-177 in a single dose for 3 months.

Results

Following the treatment, significant improvements were observed in the levels of bilirubin, % of prothrombin and % of albumin.

EXAMPLE 7

Activity in Compensated Hepatic Cirrhosis

Clinical trial in 11 patients diagnosed as having compensated hepatic cirrhosis and treated with 720 mg/day of A-177 in two 360 mg doses for 3 months.

Results

Following the treatment, significant improvements were observed in the serum levels of bilirubin, % of prothrombin and GPT, and in thrombocytopoiesis.

The embodiments of the invention in which an exclusive property or privilege is claimed are defined as follows:

1. A process for the treatment of hepatopathical diseases selected from the group consisting of alcoholic hepatopathy, chronic hepatitis and hepatic cirrhosis comprising the step of orally administering to a patient a therapeutically effective amount of an oral administration unit of a zinc carbocysteinate composition.

2. The process as claimed in claim 1, wherein the percentage of zinc carbocysteinate in said oral administration unit is between 50 and 80% by weight of the composition.

3. The process as claimed in claim 1, wherein the composition is prepared, for administration, in solid form or in liquid form.

4. The process as claimed in claim 1, wherein the amount of zinc carbocysteinate administered as a daily dosage is between 100 and 1200 mg/day.

5. The process as claimed in claim 1, wherein the alcoholic hepatopathy is fatty liver, alcoholic hepatitis or alcoholic cirrhosis.

6. The process as claimed in claim 4, wherein the amount of zinc carbocysteinate administered as a daily dosage is between 150 and 400 mg/day.

* * * * *